United States Patent [19]

Bouic et al.

[11] Patent Number: 5,486,510
[45] Date of Patent: Jan. 23, 1996

[54] METHOD AND COMPOSITIONS FOR MODULATING OR CONTROL OF IMMUNE RESPONSES IN HUMANS

[75] Inventors: Patrick J. D. Bouic, Ronderbosch East; Carl F. De Vosa Albrecht, Durbanville, both of South Africa

[73] Assignee: Rooperol (NA) NV, Amsterdam, Netherlands

[21] Appl. No.: 148,504

[22] Filed: Nov. 8, 1993

Related U.S. Application Data

[62] Division of Ser. No. 857,394, Mar. 25, 1992, abandoned.

[30] Foreign Application Priority Data

Mar. 28, 1991 [ZA] South Africa ............................ 91/2349

[51] Int. Cl.⁶ .................................................... A61K 31/56
[52] U.S. Cl. .......................... 514/170; 514/825; 514/826; 514/861; 514/863
[58] Field of Search .................................... 514/863, 826, 514/825, 861, 26, 170

[56] References Cited

U.S. PATENT DOCUMENTS

| | | | |
|---|---|---|---|
| 4,188,379 | 2/1980 | Pegel | 424/182 |
| 4,254,111 | 3/1981 | Pegel et al. | 424/182 |
| 4,260,603 | 4/1981 | Pegel et al. | 424/182 |
| 5,118,671 | 6/1992 | Bombardelli et al. | 514/26 |
| 5,128,324 | 7/1992 | Walker et al. | 514/26 |

FOREIGN PATENT DOCUMENTS

| | | |
|---|---|---|
| 1365661 | 9/1974 | United Kingdom . |
| 1595247 | 8/1981 | United Kingdom . |

OTHER PUBLICATIONS

Chemical Abstracts 104:161977e (1986).
Chemical Abstracts 111:114066r (1989).

*Primary Examiner*—Glennon H. Hollrah
*Assistant Examiner*—Brian M. Burn
*Attorney, Agent, or Firm*—Young & Thompson

[57] ABSTRACT

A mixture of β-sitosterol glucoside and β-sitosterol is administered to persons for the modulation or control of immune responses. The two compounds may be added in admixture or sequentially. Diseases such as viral and bacterial infections, autoimmune diseases, psoriasis, ezcema, asthma, cancer may be treated.

12 Claims, 2 Drawing Sheets

METHOD AND COMPOSITIONS FOR MODULATING OR CONTROL OF IMMUNE RESPONSES IN HUMANS

This application is a division, of application Ser. No. 07/857,394, filed Mar. 25, 1992, now abandoned.

FIELD OF INVENTION

This invention relates to methods and compositions for the modulation or control of immune responses in man and has particular utility in normalizing the immune function in man.

BACKGROUND OF THE INVENTION

The term "immunomodulation" denotes an intended physical or chemical alteration in the function of a host's immune system. The distinction is made between manipulations which cause a decrease and others which cause an increase in number and/or function of immune mechanisms. The desire and necessity to artificially control immune responses were born during the advent of clinical transplantations in the years 1965–75 when the immunologists were faced with the daunting task of preventing graft rejections. Hence was born the era of "Biological Response Modifiers (BRM's)" which can be classed as either immunosuppressive or immunostimulatory. A special subgroup of the latter exerts its stimulatory effects only on defective immune mechanisms and directs them towards normalization. Such substances are termed "immune restorative agents".

In the past, living and attenuated micro-organisms, autologous and heterologous proteins and injections of animal organ preparations were used with the aim of restoring an impaired defence mechanism. At present, thymic peptides, synthetic low molecular weight compounds, chemically modified nucleotides. polysaccharides from fungi and especially, some plant extracts are also used for the same purpose.

The recently reviewed interest in the immunomodulators arose from their potential therapeutic use in several clinical situations including:
a) chronic bacterial and/or viral infections
b) immune dysfunction
c) immune deficiency syndromes
d) tumours Although an extensive search for plant derived natural products with immunostimulatory/immunosuppressive activities is currently under way, very few such substances have entered the market.

Biological activities of some steryl glycosides have been investigated such as their effects on complement activation and their anti-inflammatory activity. The steryl glycosides, also known as phytosterolins, include the glycosides of β-sitosterol, stigmasterol, campesterol and the like, but the majority of the work has been carried out with β-sitosterol glucoside and its aglycone. β-sitosterol glucoside is obtained from a variety of plant material extracts in the form of a mixture containing, in most cases, not less than 60% of β-sitosterol glucoside with other steryl glycosides and in this specification the term β-sitosterol glucoside (which is abbreviated to BSSG) can mean either the substance itself or a mixture thereof with the other steryl glycosides. The same applies to the aglycone β-sitosterol (abbreviated to BSS in this specification).

THE INVENTION

A method for modulation or control of immune responses in the treatment of man which includes the step of administering a predetermined amount of a phytosterol and phytosterolin such as BSS and BSSG.

In one form of the invention BSS or BSSG is administered for the purpose of potentiating the function of T-cells. The potentiation effect, as seen in vitro, is exerted down to extremely low concentrations (about 150 molecules BSS per T-cell or about 10 molecules of BSSG per T-cell).

In an example of the invention BSS and BSSG are added to an in vitro culture sequentially, either with BSS administration first in which case the function of T-cells is inhibited, or when BSSG is administered first there is an excellent potentiation of the T-cells.

In a preferred form of the invention pertaining to in vitro data, an intimate mixture of BSS and BSSG is administered and results in an even greater potentiation of T-cells, with BSS in a 10 to 500 fold excess to BSSG. The preferred BSS:BSSG ratio is between 1:1 and 500:1.

In another form of the invention, BSS+BSSG is added to B-cells in vitro and this results in inhibition of the proliferative responses of the B-cells as measured by the incorporation of a radioactive isotope into the DNA of proliferating cells.

In a further form of the invention pertaining to in vitro data, BSS or BSSG or a BSS/BSSG mixture is administered for the purpose of enhancing NK cell activity either on its own or, more preferably, with IL-2.

In yet a further form of the invention, an intimate mixture of BSS+BSSG is added to T-cells which have been activated in vitro and the expression of membrane activation antigens (IL-2 receptor and HLA-DR) is measured. Under such conditions, the T-cells express higher levels of the activation antigens and simultaneously, secrete significantly more of the T-cell derived lymphokines IL-2 and Gamma Interferon.

In a trial, 5 healthy volunteers ingested 6 mg of BSSG per day and their T-cell functions were determined at time zero (baseline) and again after 6 weeks. The results of this trial show that after 6 weeks of BSSG intake, all 5 volunteers exhibit enhanced T-cell responses measured as the proliferative capabilities in vitro. These results are reported below.

Other studies conducted with the mixture BSS+BSSG on healthy volunteers show that, compared to placebo-controlled individuals, those having ingested capsules containing BSS+BSSG in a ratio of 100:1 precipitated onto talcum powder exhibit enhanced T-cell responses in vitro. The results of these studies in healthy individuals are reported below.

Furthermore, several anecdotal cases of patients treated with the mixture containing BSS+BSSG show that the compounds have important immunomodulatory properties. Such cases include: one case of Hashimoto's thyroiditis with raised anti-thyroglobulin autoantibodies reverting to seronegativity after 6 weeks of treatment; one case of severe atopic eczema totally cleared of the eczema after a month of treatment; several cases of psoriasis showing significant improvement of their lesions as measured by the PASI scoring system; and several arthritics exhibiting clinical improvement with treatment. These cases are presented below. In addition successful case histories for the treatment of asthma and cancer are presented.

DETAILED DESCRIPTION OF THE DRAWINGS

Figure 1:
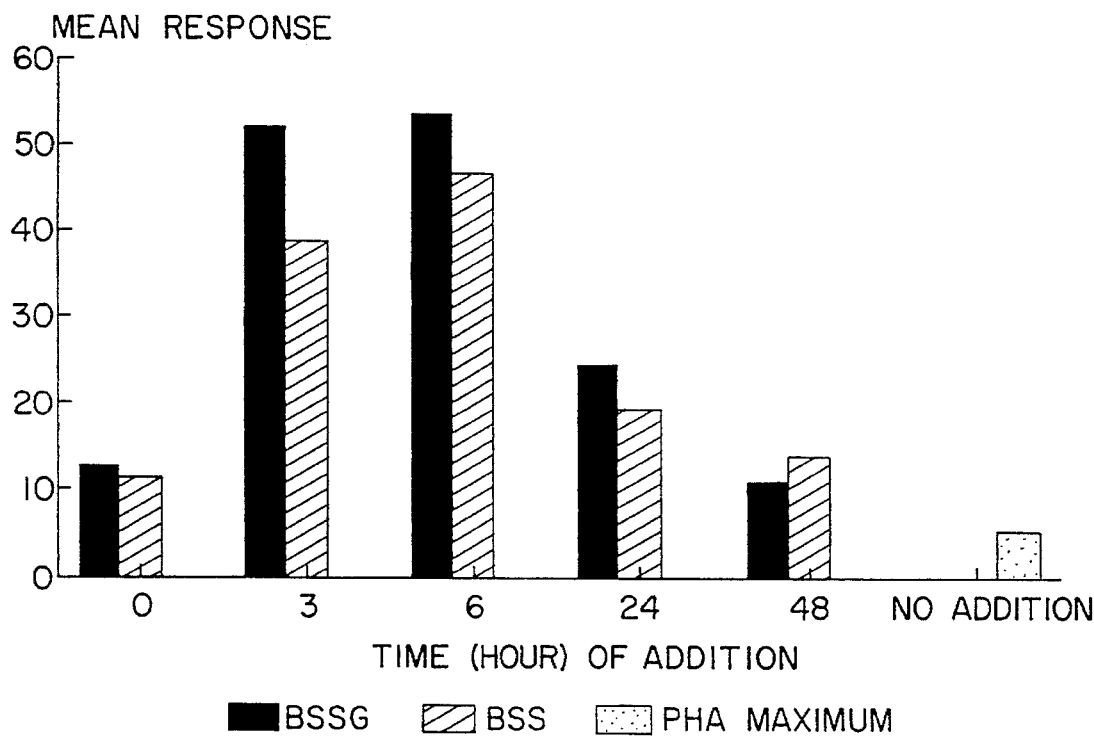
FIG. 1 is a graph of the kinetics of BSSG and BSS effects on T-cells.

In FIG. 1, T-cells were stimulated with suboptimal doses of PHA and at different times during the culture period, BSS or BSSG (10 fg/ml) was added to the culture wells and the proliferative response at 72 hours was measured.

Figure 2:
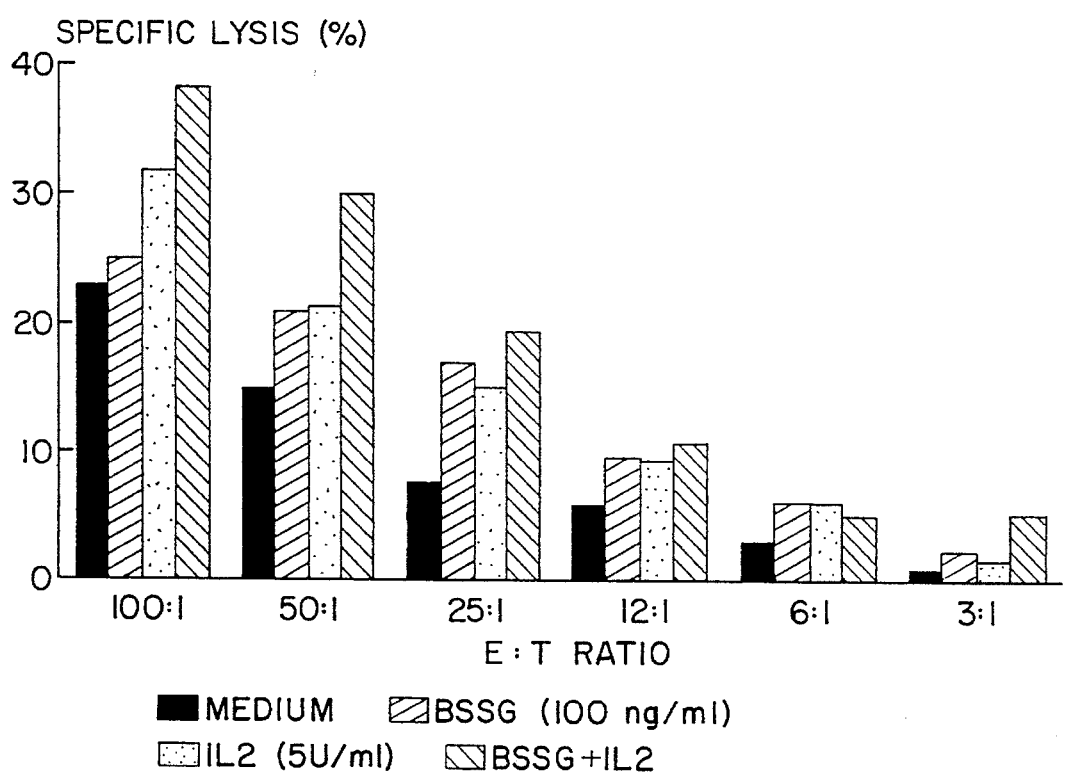
FIG. 2 is a graph of the effects of BSSG +/− IL-2 on NK cell activity.

In FIG. 2, NK cells were incubated with either IL-2 (5 U/ml) or BSSG (100 ng/ml) or BSSG+IL-2 and thereafter, their cytotoxicity was measured against K562 cells. The results are expressed as the specific lysis of the target cells at different effector to target cell ratios.

Figure 3:
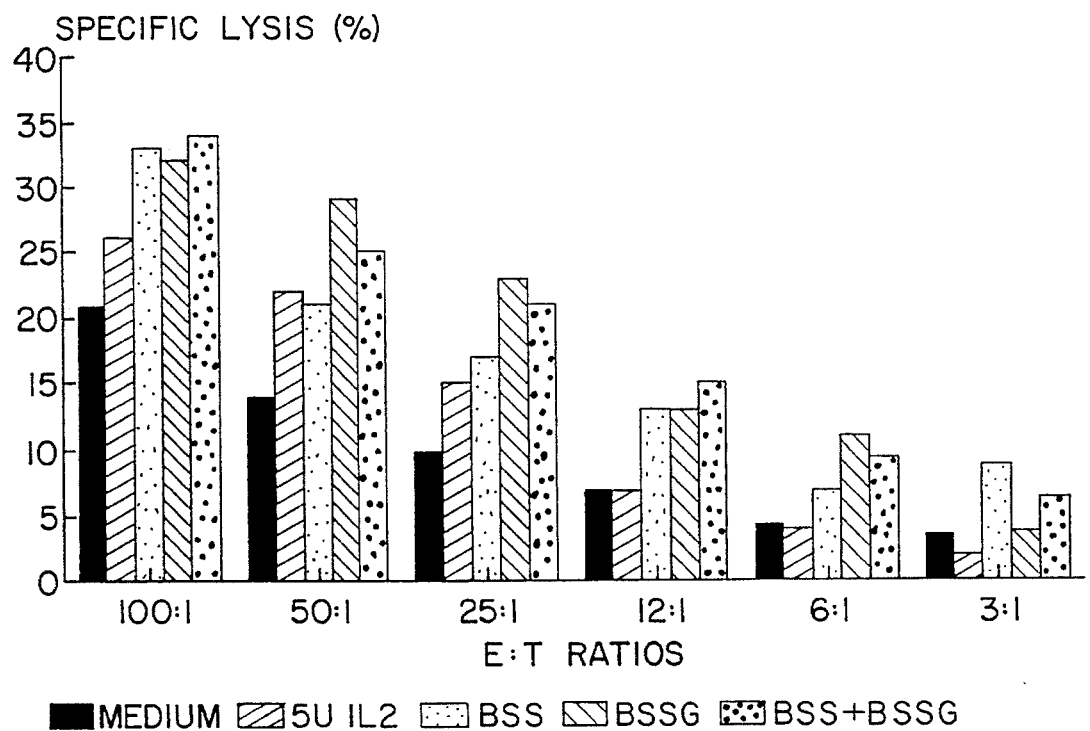
FIG. 3 is a graph of the effects of BSS+BSSG on NK cell activity.

In FIG. 3, NK cells were incubated with a mixture of BSS+BSSG (ratio of 1:1, concentration of 100 ng/ml) and their cytotoxic activity was measured against K562 cells.

Figure 4:
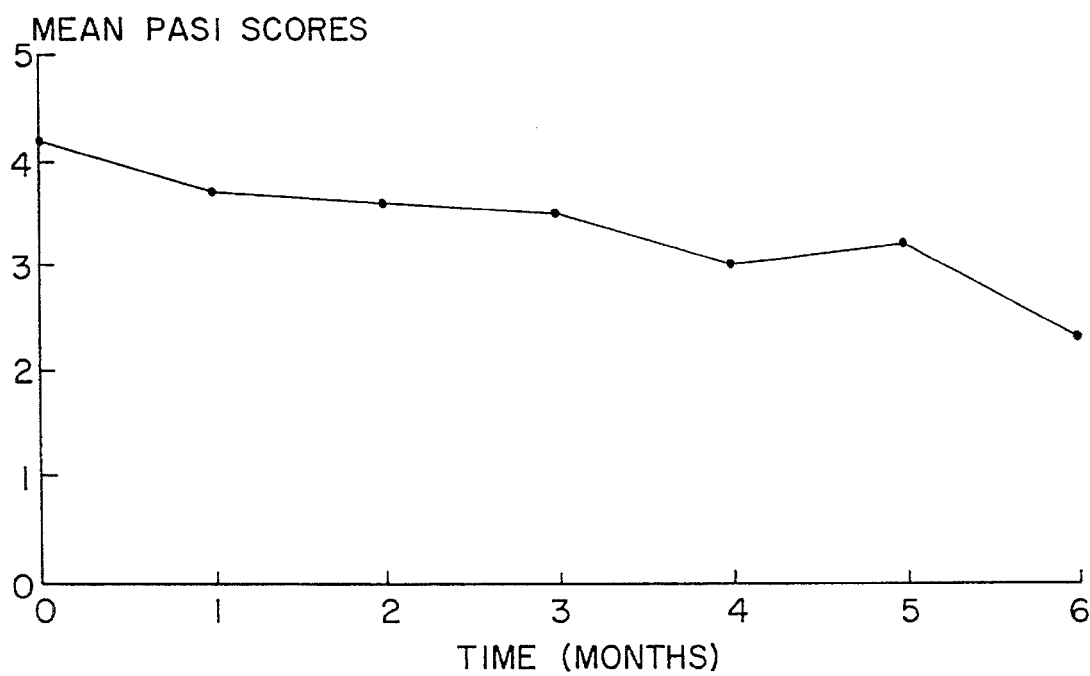
FIG. 4 is a graph of mean PASI scores of psoriasis patients treated with BSS+BSSG (20 mg+0.2 mg capsules) over time.

In FIG. 4, ten psoriasis patients were treated with capsules containing 20 mg BSS and 0.2 mg BSSG (initially three capsules per day and then with eight capsules per day) and their PASI scores were determined at monthly intervals.

TECHNICAL INFORMATION PERTAINING TO RESULTS OBTAINED FROM ADDING BSS AND/OR BSSG TO HUMAN T-CELLS, B-CELLS AND NK CELLS

Solubilization of BSS and BSSG

BSS and BSSG were always made up in 100% Dimethyl sulphoxide (DMSO). The stock solution was subsequently diluted in 100% Fetal Calf serum (FCS) and this working solution was further diluted 1:10 into the wells of the microtiter plates or into the culture tubes containing the cell suspension in culture medium and antibiotics. The final concentrations were thus 1% DMSO and 10% FCS. All concentrations of the phytosterol and phytosterolin indicated are final concentrations (on per ml basis) within the culture wells.

Isolation of Mononuclear Cells from Peripheral Blood

Venous blood, collected in preservative-free lithium heparin tubes was obtained from healthy laboratory personnel. The blood was diluted 50% with Tris-buffered RPMI 1640 culture medium and layered onto Lymphoprep. After centrifugation at 400 g for 25 mins, the total mononuclear cell fraction was collected at the interface and the cells were washed 3 times with the Tris-RPMI by centrifugation.

Preparation of T-cells by Rosette Formation

The T-cells were prepared from the mononuclear cell fraction using the technique of rosettes. Briefly, 3–5×10$^6$ mononuclear cells, made up in RPMI and 10% FCS, were mixed with an equal volume of 1% sheep red blood cells (SRBC) treated with AET (2-amino-ethylisouronium bromide). After overnight incubation at 4° C., the rosettes were separated by density centrifugation. The rosetting cells (T-cells) were recovered by lysis of the red blood cells and such cells were subsequently used as an enriched population of T-cells. The non-rosetting cells recovered at the interface of the density gradient were used as a source of enriched B-cells.

Lymphoproliferative Assays

The effects of BSS and BSSG on T-cell proliferation in vitro was measured as the 3H-Thymidine incorporation after 72 hours of culture at 37° C. and 5% $CO_2$. As mitogen, PHA (Phytohemagglutinin) was used as a pure T-cell mitogen. Suboptimal concentrations of the mitogen (determined from the dose-response curve) was used and all cultures were conducted in quadruplicates. Results were expressed as Mean dpm±SEM of quadruplicate determinations. The concentrations of all substances added to culture wells are per ml of fluid.

The effects of BSS and BSSG on B-cell proliferation in vitro was measured as above but the mitogen used was a preparation of Staphyloccocus Protein A used at sub-optimal concentration determined from the respective dose-response curve.

NK Cell Assays

The NK cell activity was measured as the amount of $^{51}$Chromium released in the supernatant by the cancer cell line K562. Briefly, the K562 cells were preloaded with $^{51}$Chromium and after several wasties, were mixed with defined ratios of effector cells prepared from peripheral blood (ratios: 100:1; 50:1; 25:1; 12:1; 6:1 and 3:1 :: E:T). After 4 hours incubation at 37° C. and 5% $CO_2$ the plates were centrifuged and 100 μl of the supernatants were counted to determine the amount of radioactivity present. Spontaneous release and maximal release of the isotope were determined in the respective control wells.

The results were expressed as % Specific Lysis determined as follows:

$$\% \text{ Spec Lysis} = \frac{\text{Test dpm} - \text{Spontaneous dpm}}{\text{Max dpm} - \text{Spontaneous dpm}} \times 100$$

The effects of BSSG±IL-2 were measured by incubating the effector cells for 16 hours at 37° C. and 5% $CO_2$ prior to their use in the assay.

Measurement of Membrane Activation Antigen Expression by Flow Cytometry

One million enriched T-cells were incubated for 24 hours at 37° C. and 5% $CO_2$ either in complete medium (unstimulated cells) or with PHA at sub-optimal concentrations (stimulated cells). In certain cultures, a mixture of BSS+BSSG at a ratio of 100:1 and final concentration of 1 μg was added to the cells in order to measure the effects of the phytosterols and phytosterolins on the expression of membrane antigens. Following the incubation period, the cells of each culture tube were washed in RPMI Tris buffer and subsequently incubated with an aliquot of monoclonal antibody specific for the Interleukin 2 receptor (IL2-R) or the HLA-DR antigen. These antibodies were directly conjugated fluoresceinated antibodies commercially available. After 3 final washes, the cells were analysed on a flow cytometer (FACScan, Becton Dickinson) equipped with the analytical software programme Lysis II.

Measurement of Lymphokine Secretion by T-cells

One million enriched T-cells were incubated with medium or PHA at sub-optimal doses in the absence or presence of BSS+BSSG (100:1 ratio; 1 μg/ml final concentration) as above. Forty eight hours later, the culture tubes were spun down and the supernatants were analysed for their Interleukin 2 and Gamma Interferon contents. For this, a commercial radioimmunoassay kit was used for the determination of IL-2 content (range 0–60 IU/ml) while the content in Gamma Interferon was determined by an in-house enzyme-linked immunosorbent (ELISA) method using recombinant antigen and commercial monoclonal antibodies specific for the factor. This assay has a sensitivity of 1 IU/ml and a working range of 1–500 IU/ml.

RESULTS

Effects of BSS on T-cells in Vitro

Experiments were carried out in order to determine whether BSS had any effects on T-cells. For this BSS was tested in proliferative assays where PHA was used as a stimulus for T-cells. Table I shows the results obtained with BSS in a concentration range of 10 pg/ml to 1 ag/ml. As can be seen, the proliferative responses of T-cells in the presence of BSS are significantly enhanced. This potentiating effect is exerted down to the lowest concentration of 10 fg/ml and thereafter this effect is no longer measurable. Previous experiments showed that BSS had an enhancing activity between the concentrations of 10 μg/ml to 10 fg/ml (data not shown). When one takes into consideration that at 10 fg/ml, there are $15 \times 10^6$ molecules of BSS available to $1 \times 10^5$ T-cells, one can speculate that the entrancing activity of BSS is exerted by 150 molecules of BSS per T-cell.

no significant effect on the response of T-cells to PHA. From previous data not shown, it can be said that BSSG exerts this potentiating effect between the concentrations of 10 μg/ml to 1 fg/ml.

Furthermore, 1 fg/ml of BSSG represents $1 \times 10^6$ active molecules available to $1 \times 10^5$ T-cells. This means that each T-cell can theoretically bind 10 molecules of BSSG. Whether BSSG binds to the same receptor as BSS is at present unknown but preliminary data showed that resting T-cells (non-activated) actively bind radio-labelled BSSG and this binding is increased 4–5 fold once the T-cells are pre-activated.

TABLE I

EFFECT OF BSS ON T-CELLS IN VITRO:
T-cells were stimulated with sub-optimal doses of PHA in the presence/absence of the phytosterol (BSS) in a concentration range of 10 pg/ml to 1 ag/ml and the proliferative response was measured as Thymidine uptake.

|  |  | Mean dpm ± SEM | "p" |
|---|---|---|---|
| T-cells + med |  | 95 ± 4 | na. |
| T-cells + med + PHA |  | 8304 ± 657 | na. |
| T-cells + med + PHA + BSS | 10 pg/ml | 24614 ± 2477 | *<.001 |
| T-cells + med + PHA + BSS | 1 pg/ml | 21519 ± 799 | *<.001 |
| T-cells + med + PHA + BSS | 100 fg/ml | 17970 ± 1571 | *<.01 |
| T-cells + med + PHA + BSS | 10 fg/ml | 17261 ± 698 | *<.01 |
| T-cells + med + PHA + BSS | 1 fg/ml | 7984 ± 188 | NS |
| T-cells + med + PHA + BSS | 100 ag/ml | 8624 ± 418 | NS |
| T-cells + med + PHA + BSS | 10 ag/ml | 8254 ± 429 | NS |
| T-cells + med + PHA + BSS | 1 ag/ml | 8487 ± 391 | NS |

* = enhancement of proliferative response

Effects of BSSG on T-cells in vitro

BSSG had very similar effects to BSS on the proliferation of T-cells in vitro. Table II shows that BSSG potentiated the proliferative response of T-cells in the concentration range of 10 pg/ml to 1 fg/ml. Lower concentrations of BSSG had

TABLE II

EFFECT OF BSSG ON T-CELLS IN VITRO:
T-cells were stimulated with sub-optimal doses of PHA in the presence/absence of the phytosterolin (BSSG) in a concentration range of 10 pg/ml to 1 ag/ml. The proliferative response was measured as Thymidine uptake.

|  |  | Mean dpm + SEM | "p" |
|---|---|---|---|
| T-cells + med |  | 120 ± 5 | na. |
| T-cells + med + PHA |  | 9704 ± 154 | na. |
| T-cells + med + PHA + BSSG | 10 pg/ml | 30083 ± 1312 | *<.001 |
| T-cells + med + PHA + BSSG | 1 pg/ml | 24421 ± 1691 | *<.001 |

TABLE II-continued

EFFECT OF BSSG ON T-CELLS IN VITRO:
T-cells were stimulated with sub-optimal doses of PHA in the presence/absence of the phytosterolin (BSSG) in a concentration range of 10 pg/ml to 1 ag/ml. The proliferative response was measured as Thymidine uptake.

|  |  | Mean dpm + SEM | "p" |
|---|---|---|---|
| T-cells + med + PHA + BSSG | 100 fg/ml | 23316 ± 1091 | *<.001 |
| T-cells + med + PHA + BSSG | 10 fg/ml | 23014 ± 1422 | *<.001 |
| T-cells + med + PHA + BSSG | 1 fg/ml | 17289 ± 941 | *<.01 |
| T-cells + med + PHA + BSSG | 100 ag/ml | 8807 ± 454 | NS |
| T-cells + med + PHA + BSSG | 10 ag/ml | 9159 ± 239 | NS |
| T-cells + med + PHA + BSSG | 1 ag/ml | 8301 ± 824 | NS |

\* = enhancement of proliferative response

Effects of BSS+BSSG Mixture on T-cells in vitro

Since BSS and BSSG individually enhanced the proliferative response of T-cells to PHA in vitro, it was of interest to determine whether the two compounds, when added to cultures of T-cells, would have additive enhancing effects. For this, experiments were carried out where BSS was added first in increasing quantities relative to the BSSG which was added subsequently. The results of a typical experiment are shown in Table III. As can be seen from these results, BSS and BSSG, when individually added to stimulated T-cells, significantly enhanced the proliferative responses, thereby confirming previous observations. However, when added together to the cultures, a dramatic inhibitory effect was observed, irrespective of the relative ratio of BSS to BSSG. This seemed to indicate that BSS could possibly act as an antagonist to BSSG and that, perhaps, competitive binding for the same receptor could take place. However, in vivo data seemed to contradict the in vitro data.

TABLE III

EFFECT OF BSS + BSSG MIXTURE ON T-CELLS IN VITRO:
T-cells were cultured with sub-optimal doses of PHA in the presence/absence of BSSG alone or BSS alone. Certain cultures received both BSS and BSSG (various ratios of 1:1 up to 200:1; BSS:BSSG respectively) with BSS being added to the cultures first.

|  |  | Mean dpm ± SEM | "p" |
|---|---|---|---|
| T-cells + med |  | 139 ± 12 | na. |
| T-cells + med + PHA |  | 70011 ± 4083 | na. |
| T-cells + med + PHA + BSSG | 1 fg/ml | 118669 ± 3988 | *<.001 |
| T-cells + med + PHA + BSSG | 5 fg/ml | 111404 ± 5979 | *<.01 |
| T-cells + med + PHA + BSS | 10 fg/ml | 105761 ± 5472 | *<.01 |
| T-cells + med + PHA + BSS | 20 fg/ml | 119362 ± 1273 | *<.001 |
| T-cells + med + PHA + BSS | 50 fg/ml | 88391 ± 7519 | *<.01 |
| T-cells + med + PHA + BSS + BSSG | 1 fg/ml<br>1 fg/ml | 168 ± 30 | <.001 |
| T-cells + med + PHA + BSS + BSSG | 4 fg/ml<br>1 fg/ml | 139 ± 14 | <.001 |
| T-cells + med + PHA + BSS + BSSG | 5 fg/ml<br>5 fg/ml | 145 ± 22 | <.001 |
| T-cells + med + PHA + BSS + BSSG | 20 fg/ml<br>5 fg/ml | 126 ± 24 | <.001 |
| T-cells + med + PHA + BSS + BSSG | 50 fg/ml<br>5 fg/ml | 117 ± 20 | <.001 |
| T-cells + med + PHA + BSS + BSSG | 100 fg/ml<br>5 fg/ml | 146 ± 37 | <.001 |
| T-cells + med + PHA + BSS + BSSG | 250 fg/ml<br>5 fg/ml | 106 ± 14 | <.001 |
| T-cells + med + PHA + BSS + BSSG | 500 fg/ml<br>5 fg/ml | 113 ± 34 | <.001 |
| T-cells + med + PHA + BSS + BSSG | 1000 fg/ml<br>5 fg/ml | 258 ± 83 | <.001 |

\* = enhancement of proliferative response

Further experiments were therefore carried out to determine whether increasing quantities of BSSG, relative to BSS, would have similar effects in vitro. The results of a typical experiment are shown in Table IV. Surprising results were obtained in that when BSSG is increased relative to BSS, the proliferative response is significantly enhanced. The only difference to which these confusing results could be attributed is the order of addition of the two compounds: in the former experiment (Table III), BSS was added first followed by the respective dose of BSSG. In the latter experiment (Table IV), BSSG was added first followed by BSS.

TABLE IV

EFFECT OF BSSG + BSS MIXTURE ON T-CELLS IN VITRO:
T-cells were stimulated with sub-optimal doses of PHA in the presence/absence of BSS alone, BSSG alone or BSS + BSSG added to the cultures. When tested together, various ratios were used (ratios of 1:1 up to 200:1; BSSG relative to BSS) and the BSSG was added to the cultures first

|  |  | Mean dpm ± SEM | "p" |
|---|---|---|---|
| T-cells + med |  | 84 ± 19 | na. |
| T-cells + med + PHA |  | 13989 ± 647 | na. |
| T-cells + med + PHA + BSS | 1 fg/ml | 48439 ± 2831 | *<.001 |
| T-cells + med + PHA + BSS | 5 fg/ml | 44042 ± 4055 | *<.001 |
| T-cells + med + PHA + BSSG | 10 fg/ml | 46488 ± 2452 | *<.001 |
| T-cells + med + PHA + BSSG | 20 fg/ml | 46778 ± 983 | *<.001 |
| T-cells + med + PHA + BSSG | 50 fg/ml | 50158 ± 3149 | *<.001 |
| T-cells + med + PHA + BSSG + BSS | 1 fg/ml  1 fg/ml | 81123 ± 6647 | *<.001 |
| T-cells + med + PHA + BSSG + BSS | 4 fg/ml  1 fg/ml | 76543 ± 2406 | *<.001 |
| T-cells + med + PHA + BSSG + BSS | 5 fg/ml  5 fg/ml | 74059 ± 2971 | *<.001 |
| T-cells + med + PHA + BSSG + BSS | 20 fg/ml  5 fg/ml | 80118 ± 2499 | *<.001 |
| T-cells + med + PHA + BSSG + BSS | 50 fg/ml  5 fg/ml | 76339 ± 668 | *<.001 |
| T-cells + med + PHA + BSSG + BSS | 100 fg/ml  5 fg/ml | 69786 ± 2105 | *<.001 |
| T-cells + med + PHA + BSSG + BSS | 250 fg/ml  5 fg/ml | 67287 ± 3242 | *<.001 |
| T-cells + med + PHA + BSSG + BSS | 500 fg/ml  5 fg/ml | 61402 ± 1881 | *<.001 |
| T-cells + med + PHA + BSSG + BSS | 1000 fg/ml  5 fg/ml | 37998 ± 1768 | *<.001 |

* = enhancement of proliferative response

Since compositions containing both BSS and BSSG (BSS:BSSG :: 10:1 and 10:0.25 in mg per oral dose were used successfully, the following experiment was therefore decided upon. Certain cultures would receive first 10 fg/ml of BSS followed by 10 fg/ml of BSSG. Other cultures would receive 10 fg/ml of BSSG followed by 10 fg/ml of BSS; and the third set of cultures would receive 10 fg/ml BSS+10 fg/ml BSSG, the two compounds being mixed prior to addition to the cells. Results of a typical experiment are shown in Table V. As can be seen, when BSS or BSSG is added individually to the cultures significant enhancement of the response results. In the mixing experiments, when BSSG is added first, enhancement results. What is interesting to note is the fact that when BSS and BSSG are mixed prior to addition to the cells, enhancement of the proliferative response results and this enhancement is even more pronounced.

TABLE V

EFFECT OF BSS + BSSG ON T-CELLS IN VITRO:
EFFECT OF ORDER OF ADDITION:
T-cells were stimulated with PHA at sub-optimal doses in the presence/absence of BSS alone, BSSG alone or BSS mixed with BSSG at a ratio of 1:1. In the mixing, care was taken to add either the BSS first, or the BSSG first or the two compounds were mixed prior to adding to the culture.

|  |  | Mean dpm ± SEM | "p" |
|---|---|---|---|
| T-cells + med |  | 127 ± 4 | na. |
| T-cells + PHA |  | 18043 ± 798 | na. |
| T-cells + PHA + BSS | 10 fg/ml | 72590 ± 3740 | *<.001 |
| T-cells + PHA + BSSG | 10 fg/ml | 84887 ± 4930 | *<.001 |
| T-cells + PHA + BSS + BSSG (1st the BSS) |  | 6944 ± 243 | <.001 |
| T-cells + PHA + BSSG + BSS (1st the BSSG) |  | 68558 ± 2436 | *<.001 |
| T-cells + PHA + BSS + BSSG (together) |  | 85877 ± 5841 | *<.001 |

* = enhancement of proliferative response

It can therefore be concluded from these experiments that both BSS and BSSG individually are immunostimulatory in nature and that the mixture BSS+BSSG has potent immunomodulatory properties vis-a-vis T-cells.

Kinetics of BSSG and BSS Effects on T-cells in vitro

Since the enhancing effects of BSS and BSSG were being measured in a proliferative assay (72 hours of culture), it was important to determine at which phases of the proliferative response these compounds were exerting their effect(s). In other words, were the T-cells being affected during early events such as acquisition of activation antigens and/or secretion of growth factors (IL-2; γ-IFN; etc) or were the late events (mitosis, etc) being influenced? For this purpose, the following experiments were conducted:- T-cells were stimulated with PHA and at different times during the culture period (0;3;6;24 and 48 hrs). An amount of 10 fg/ml of BSS or BSSG was added and the end point proliferative response was measured as $^3$H-Thymidine uptake by the cells. Representative results of such experiments are presented in Table VI. As can be seen, addition of BSS or BSSG to stimulated T-cells from zero time has significant enhancing consequences but these effects are maximal at time=6 hrs and thereafter decreases back to normal proliferative levels by 48 hrs. These results are presented graphically in FIG. 1. These results indicate that the potentiated proliferative response of T-cells measured at 72 hrs probably arises as a result of enhanced or up-regulation of events taking place early on during the activation cycle of the T-cells—these events could include the up-regulation of new membrane receptors such as the interleukin—2 receptor (IL2-R) or HLA-Class II antigen (HLA-DR) or the expression of other activation antigens such as the Transferrin receptor (Tf). The possibility that the up-regulation of growth factor synthesis and secretion also takes place cannot be excluded (these growth factors such as IL-2; γ-IFN; etc are essential in a proliferative response of T-cells).

TABLE VI

KINETICS OF BSSG AND BSS EFFECTS ON T-CELLS IN VITRO:
T-cells were stimulated with sub-optimal doses of PHA and at different times during the culture period, BSSG (10 fg/ml) or BSS (10 fg/ml) was added. The end point, proliferative response was measured at 72 hours of culture.

|  | Mean dpm ± SEM | "p" |
|---|---|---|
| T-cells + med | 60 ± 10 | na. |
| T-cells + PHA | 5635 ± 939 | na. |
| T-cells + PHA + BSSG (0 hr) | 12663 ± 933 | *<.01 |
| T-cells + PHA + BSSG (3 hr) | 52200 ± 1579 | *<.001 |
| T-cells + PHA + BSSG (6 hr) | 53709 ± 3006 | *<.001 |
| T-cells + PHA + BSSG (24 hr) | 24563 ± 749 | *<.001 |
| T-cells + PHA + BSSG (48 hr) | 11110 ± 524 | *<.01 |
| T-cells + PHA + BSS (0 hr) | 11292 ± 486 | *<.01 |
| T-cells + PHA + BSS (3 hr) | 38743 ± 480 | *<.001 |
| T-cells + PHA + BSS (6 hr) | 46623 ± 1617 | *<.001 |
| T-cells + PHA + BSS (24 hr) | 19464 ± 1743 | *<.001 |
| T-cells + PHA + BSS (48 hr) | 14087 ± 819 | *<.001 |

* = enhancement of proliferative response

Effect of BSS+BSSG on the Expression of Membrane Activation Antigens by T-cells in vitro Enriched T-cells were incubated with or without a mitogen and the expression of activation antigens was measured by flow cytometry using monoclonal antibodies. Results of a typical experiment are presented and as can be seen from Table VII, activated T-cell express higher levels of the antigens examined. However, when a BSS+BSSG mixture at a ratio of 100:1 and final concentration of 1 μg/ml is added simultaneously to the mitogen, even higher positivity of the cells results. In the case of HLA-DR antigen, the mixture of BSS+BSSG enhances the expression by as much as 13% while for the IL2-R, this is enhanced by 15% (Table VII).

TABLE VII

EFFECT OF BSS + BSSG ON EXPRESSION OF ACTIVATION ANTIGENS BY T-CELLS:
T-cells were cultured for 24 hours in the presence of PHA and a mixture of BSS + BSSG (ratio of 100:1 and concentration of 1 μg/ml) was added to certain cultures. Following the culture period, the cells were stained with monoclonal antibodies specific for the IL2-R or HLA-DR antigens and analysed by flow cytometry.

| | % Positivity | | |
|---|---|---|---|
| Stimulus | NS Staining* | IL2-R | HLA-DR |
| Medium | 3 | 2 | 6 |
| PHA only | 0 | 11 | 22 |
| PHA + BSS + BSSG (100:1; 1 μg/ml) | 1 | 26 | 35 |

*denotes non-specific staining of the cell preparation by a control antibody of similar isotype to the specific monoclonal antibodies.

Effect of BSS+BSSG on Gamma Interferon Secretion by T-cells in vitro

When enriched T-cells were cultured with PHA in the presence of BSS+BSSG at a ratio of 100:1 and a final concentration of 1 μg/ml, enhanced secretion of Gamma Interferon resulted (Table VIII). This enhancement of Gamma Interferon secretion was more pronounced than in cells which had been stimulated with optimal doses of the mitogen only. Unstimulated cells released very little of the growth factor Gamma Interferon in vitro.

TABLE VIII

EFFECT OF BSS + BSSG ON GAMMA INTERFERON SECRETION FROM T-CELLS IN VITRO:
T-cells were cultured with PHA at optimal or sub-optimal doses and certain cultures received sub-optimal doses of PHA plus a mixture of BSS + BSSG (ratio of 100:1 and final concentration of 1 μg/ml). Following the culture period, the supernatants were assayed for their contents in Gamma Interferon.

| Stimulus | Gamma Interferon/10$^6$ cells IU/ml |
|---|---|
| Medium | 3.3 |
| PHA (sub-optimal dose) | 5.5 |
| PHA (optimal dose) | 29.2 |
| PHA (sub-optimal dose) + BSS/BSSG (100:1; 1 μg/ml) | 83.3 |

Effect of BSS+BSSG on IL-2 Secretion from T-cells in vitro

Similar to the results reported above, the addition of BSS+BSSG at a ratio of 100:1 and at a final dose of 1 μg/ml to stimulated enriched T-cells resulted in enhanced IL-2 secretion in vitro. Cells which had been sub-optimally stimulated released a little more than cells which had been incubated in medium alone. Maximally stimulated cells released significantly more of the factor but this secretion was not comparable to the secretion which occurred when cells (sub-optimally stimulated) were co-cultured with the mixture of phytosterols and phytosterolins, Results of a typical experiment are presented in Table IX.

TABLE IX

EFFECT OF BSS + BSSG ON THE SECRETION OF IL-2 FROM T-CELLS IN VITRO:
T-cells were cultured with PHA (optimal or sub-optimal doses) and a mixture of BSS + BSSG (ratio of 100:1; concentration of 1 µg/ml) was added to certain cultures. Following the incubation period, the supernatants were assayed for their IL-2 contents.

| Stimulus | IL-2 Secretion (IU/ml)/$10^6$ cells |
|---|---|
| Medium | 0.7 |
| PHA (sub-optimal) | 0.9 |
| PHA (optimal) | 1.1 |
| PHA (sub-optimal) + BSS + BSSG (100:1; 1 µg/ml) | 1.4 |

Effect of BSS OR BSSG on B-cell Proliferation in vitro

Non-rosetting cells (enriched B-cells) prepared from peripheral blood lymphocytes of normal donors were cultured in vitro with a pure B-cell mitogen Staphyloccocus Protein A (Prot. A) together with various doses of either BSS or BSSG in a range of 10 µg/ml to 100 pg/ml. As can be seen from Table X, both BSS and BSSG significantly inhibited the proliferative responses of B-cells in vitro and although the inhibitory effects of the phytosterols were not titered out, the implication of this inhibitory activity shall be discussed later in relation to certain anecdotal cases.

TABLE X

EFFECT OF BSS OR BSSG ON B-CELL PROLIFERATION IN VITRO:
Enriched B-cells were stimulated with Protein A at sub-optimal doses and BSS (concentration range of 10 µg/ml to 100 pg/ml) or BSSG in a similar concentration range was added to certain cultures. The response measured as Thymidine uptake.

| | | Mean cpm ± SEM | "p" |
|---|---|---|---|
| B-cells + med | | 377 ± 9 | na |
| B-cells + med + Prot A | | 1155 ± 31 | na |
| B-cells + med + Prot A + BSS | 10 µg/ml | 543 ± 33 | <.001 |
| B-cells + med + Prot A + BSS | 1 µg/ml | 524 ± 37 | <.001 |
| B-cells + med + Prot A + BSS | 100 ng/ml | 474 ± 32 | <.001 |
| B-cells + med + Prot A + BSS | 10 ng/ml | 692 ± 87 | <.001 |
| B-cells + med + Prot A + BSS | 1 ng/ml | 755 ± 18 | <.001 |
| B-cells + med + Prot A + BSS | 100 pg/ml | 767 ± 22 | <.001 |
| B-cells + med | | 369 ± 20 | na |
| B-cells + med + Prot A | | 1135 ± 33 | na |
| B-cells + med + Prot A + BSSG | 10 µg/ml | 746 ± 110 | <.02 |
| B-cells + med + Prot A + BSSG | 1 µg/ml | 737 ± 97 | <.01 |
| B-cells + med + Prot A + BSSG | 100 ng/ml | 483 ± 99 | <.001 |
| B-cells + med + Prot A + BSSG | 10 ng/ml | 447 ± 40 | <.001 |
| B-cells + med + Prot A + BSSG | 1 ng/ml | 555 ± 15 | <.001 |
| B-cells + med + Prot A + BSSG | 100 pg/ml | 560 ± 62 | <.001 |

In a single experiment, the effects of BSS or BSSG were measured in a concentration range of 10 ng/ml to 1 fg/ml and at the lowest concentration of 1 fg/ml inhibition of the proliferative responses of B-cells were still observed. These results are presented in Table XI.

TABLE XI

EFFECT OF BSS OR BSSG ON B-CELL PROLIFERATION
IN VITRO:
B-cells were stimulated with Protein A (sub-optimal dose) and BSS
(concentration range of 10 ng/ml to 1 fg/ml) or BSSG in a similar
range was added to certain cultures. The proliferative response
was measured as Thymidine uptake.

|  |  | Mean cpm ± SEM | "p" |
|---|---|---|---|
| B-cells + med |  | 183 ± 16 | na |
| B-cells + med + Prot A |  | 1491 ± 44 | na |
| B-cells + med + Prot A + BSS | 10 ng/ml | 666 ± 20 | <.001 |
| B-cells + med + Prot A + BSS | 1 ng/ml | 696 ± 14 | <.001 |
| B-cells + med + Prot A + BSS | 100 pg/ml | 798 ± 22 | <.01 |
| B-cells + med + Prot A + BSS | 10 pg/ml | 808 ± 32 | <.01 |
| B-cells + med + Prot A + BSS | 1 pg/ml | 814 ± 35 | <.01 |
| B-cells + med + Prot A + BSS | 100 fg/ml | 817 ± 29 | <.01 |
| B-cells + med + Prot A + BSS | 10 fg/ml | 921 ± 14 | <.01 |
| B-cells + med + Prot A + BSS | 1 fg/ml | 936 ± 26 | <.01 |
| B-cells + med |  | 244 ± 9 | na |
| B-cells + med + Prot A |  | 1650 ± 26 | na |
| B-cells + med + Prot A + BSSG | 10 ng/ml | 741 ± 9 | <.001 |
| B-cells + med + Prot A + BSSG | 1 ng/ml | 753 ± 20 | <.001 |
| B-cells + med + Prot A + BSSG | 100 pg/ml | 762 ± 10 | <.001 |
| B-cells + med + Prot A + BSSG | 10 pg/ml | 763 ± 13 | <.001 |
| B-cells + med + Prot A + BSSG | 1 pg/ml | 794 ± 21 | <.001 |
| B-cells + med + Prot A + BSSG | 100 fg/ml | 803 ± 25 | <.001 |
| B-cells + med + Prot A + BSSG | 10 fg/ml | 811 ± 35 | <.001 |
| B-cells + med + Prot A + BSSG | 1 fg/ml | 825 ± 15 | <.001 |

Effect of BSSG±IL-2 on NK Cell Activity

NK cells (or natural-killers) are large granular lymphocytes having highly specialised functions of lysing virally—transformed host cells or cancerous cells both in vitro and in vivo. The exact origin of these cells is highly controversial but evidence is accumulating to indicate that the NK cells represent a sub-type of Thymus-derived cells namely the T-cells.

Since it had been shown that both BSS and BSSG enhanced the proliferative response of T-cells to PHA, experiments were conducted to determine whether NK cell activity in vitro could be modulated by BSSG. At the same time, the effect of BSSG on the IL-2-enhanced NK cell activity (well-documented phenomenon) was measured. Results of a typical assay are presented in FIG. 2. Several interesting features should be highlighted from these results:
a) as shown by other authors, NK cell activity can be enhanced by IL-2.
b) BSSG, at 100 ng/ml, significantly enhances NK cell activity in vitro (especially at Effector to target ratios of 50:1; 25:1; 12:1 and 6:1).
c) This enhancement is even more pronounced when BSSG is added simultaneously with IL-2.

However it must be pointed out that the enhancement by BSSG, of NK cell activity In vitro is not ubiquitous for all blood samples tested. Indeed, it had been shown that NK cell donors who generally have a low animal-fat diet and a high phytosterol intake are those whose NK cells are not influenced by the co-culture with BSSG (data not shown). However, the same donors exhibit higher NK cell activity in vitro when compared to their counterparts who have high animal-fat and low phytosterol diets. It should be noted that a high phytosterol (BSS) intake based on a vegetarian diet is always accompanied by BSSG (approximately BSS:BSSG :: 10:1); thus, the observed effect in high phytosterol consumers (vegetarians) may be ascribed to a mixed BSS and BSSG intake.

This observation is further reinforced by the experiment presented in FIG. 3 where NK cell activity was measured in the presence of a mixture of BSS+BSSG (ratio of 1:1 and final concentration of 100 ng/ml). As can be seen, NK cell activity was enhanced in the presence of the phytosterol (BSS) on its own as well as in the presence of the phytosterolin (BSSG) relative to the medium cultures. However, the mixture of BSS+BSSG induced, at most Effector : Target cell ratios, a more significant enhancement of the NK cell activity in vitro.

TECHNICAL INFORMATION PERTAINING TO RESULTS OBTAINED IN VIVO

Volunteers 5 volunteers (healthy, laboratory personnel) were advised to take 2 mg of BSSG orally three times per day. These volunteers maintained their usual diets and blood was drawn on day zero and again 6 weeks later.

In a similar study conducted using capsules containing 0.1 mg BSSG+10 mg BSS precipitated onto 100 mg talcum (3 volunteers were advised to ingest 2 such capsules three times per day), blood samples were obtained from the volunteers at baseline (day zero) and again 4 weeks later. They were advised not to alter their diets during this period of BSS+BSSG intake. In parallel, 2 volunteers served as the control group since they were bled at the same intervals as those in the experimental group but they did not receive capsules.

Analysis of T-cell Function in vitro

The blood was processed by isolating the mononuclear cell fraction by density centrifugation as previously described. The cells were cultured for 3 days at 37° C. and 5% $CO_2$ in the presence of optimal and sub-optimal concentrations of PHA. Certain cultures received sub-optimal concentrations of PHA plus 10 ng of BSSG. T-cell function was measured as the uptake of $^3H$-Thymidine as previously described and the results were expressed as the mean dpm±SEM of quadruplicate determinations. In order to rule out possible experimental variations between runs (day zero versus 6 weeks), the cultures were set up using the same batch of mitogen and fetal calf serum.

In the case of the second study with the volunteers ingesting the BSS+BSSG capsules, the cultures were set up as described above using optimal PHA dose but the phytosterols and phytosterolins were not added to the cultures. The differences between the baseline and 4 week T-cell functions were compared statistically to determine possible changes in the in vitro reactivities.

Statistical Analysis

The results were analysed using the 2-tailed student's t-test or the Wilcoxon rank test and the levels of significant differences expressed as "p".

RESULTS

Effects of in vivo Intake of BSSG on T-cell Functions (as measured in vitro)

The function of T-cells from 5 healthy volunteers was measured on the day they began taking 6 mg of BSSG per day and again after 6 weeks. The function was measured as the proliferative responses to PHA in vitro and these preliminary results are presented in Table XII. As can be seen, all 5 volunteers showed significantly enhanced T-cell proliferative responses (measured as 3H-Thymidine uptake) after 6 weeks of 6 mg BSSG daily intake. This enhancement was shown for the optimal as well as the sub-optimal doses of PHA. As far as the responses to sub-optimal PHA doses in the presence of exogenously added BSSG (10 ng/ml) is concerned, only one volunteer (E.T.) showed an enhanced response when the baseline value was compared to the 6 week value. Two

TABLE XII

IN VITRO RESPONSES OF T-CELLS
FROM HEALTHY INDIVIDUALS
AFTER 6 WEEKS OF BSSG INTAKE (6 MG/DAY)
Peripheral blood was obtained from 5 volunteers at
baseline and again after 6 weeks
of BSSG intake (6 mg/day). Their in vitro
reactivities was measured against PHA at
optimal and sub-optimal doses and certain cultures
received sub-optimal doses of PHA
plus BSSG (10 ng/ml). The response was the Thymidine uptake.

|  | TIME = 0 dpm ± SEM | TIME = 6 wks. dpm ± SEM | "p" |
|---|---|---|---|
| A) C. A. | | | |
| C/med | 549 ± 30 | 468 ± 60 | |
| PHA (opt) | 70060 ± 854 | 137619 ± 2234 | **<.001 |
| PHA (sub-opt) | 14148 ± 764 | 57737 ± 1511 | **<.001 |
| PHA (sub-opt) + BSSG | 23609 ± 1882 | 26327 ± 2574 | NS |
| B) P. K. | | | |
| C/med | 605 ± 43 | 959 ± 280 | |
| PHA (opt) | 42310 ± 774 | 75966 ± 1156 | **<.001 |
| PHA (sub-opt) | 6739 ± 380 | 44049 ± 2117 | **<.001 |
| PHA (sub-opt) + BSSG | 8573 ± 203 | 8373 ± 1050 | NS |
| C) T. v d M. | | | |
| C/med | 276 ± 17 | 212 ± 35 | |
| PHA (opt) | 64487 ± 577 | 145711 ± 1891 | **<.001 |
| PHA (sub-opt) | 18040 ± 3519 | 60715 ± 1076 | **<.001 |

TABLE XII-continued

IN VITRO RESPONSES OF T-CELLS
FROM HEALTHY INDIVIDUALS
AFTER 6 WEEKS OF BSSG INTAKE (6 MG/DAY)
Peripheral blood was obtained from 5 volunteers at
baseline and again after 6 weeks
of BSSG intake (6 mg/day). Their in vitro
reactivities was measured against PHA at
optimal and sub-optimal doses and certain cultures
received sub-optimal doses of PHA
plus BSSG (10 ng/ml). The response was the Thymidine uptake.

|  | TIME = 0 dpm ± SEM | TIME = 6 wks. dpm ± SEM | "p" |
|---|---|---|---|
| PHA (sub-opt) + BSSG | 27329 ± 3254 | 11040 ± 654 | *<.05 |
| D) E. T. | | | |
| C/med | 423 ± 95 | 315 ± 39 | |
| PHA (opt) | 74203 ± 1512 | 128574 ± 1286 | **<.001 |
| PHA (sub-opt) | 26193 ± 502 | 71106 ± 7293 | **<.001 |
| PHA (sub-opt) + BSSG | 32649 ± 1939 | 16853 ± 1624 | *<.001 |
| E) K. S. | | | |
| C/med | 539 ± 43 | 492 ± 23 | |
| PHA (opt) | 47713 ± 1016 | 104261 ± 6725 | **<.001 |
| PHA (sub-opt) | 13351 ± 2902 | 57542 ± 1891 | **<.001 |
| PHA (sub-opt) + BSSG | 13338 ± 666 | 9727 ± 1133 | *<.05 |

**denotes enhancement of response (six week value vs. baseline)
*denotes inhibition of response (six week value vs. baseline)

other volunteers (C.A. and P.K.) showed no significant changes between their baseline and 6 week values. On the other hand, the remaining two volunteers (T.v.d.M. and K.S.) showed a minimal (although significant) inhibition of the proliferative response to a sub-optimal dose of PHA when exogenous BSSG was added to the culture wells.

These in vivo results indicate that BSSG taken orally is capable of enhancing T-cell responses in healthy individuals. Once this enhancement is achieved, exogenously added BSSG no longer exerts its effects in vitro. This is probably due to an increased plasmatic level of the phytosterol and phytosterolin (therefore an increased availability to circulating T-cells) and under such conditions, exogenously added BSSG would no longer result in potentiated T-cell responses in vitro.

Effect of in vivo BSS+BSSG Intake on T-cell Functions (as measured in vitro)

In this study 3' volunteers were asked to ingest 2 capsules containing BSS+BSSG (10 mg+0.1 mg respectively) three times daily for 4 weeks and their T-cell responses in vitro were analysed at the start of the trial and again at the end of the 4 week period. In parallel, 2 individuals served as controls since they donated blood at the same time as the experimental group but they did not receive the capsules. The results of this study are presented in Table XIII.

As can be seen the individuals receiving the BSS+BSSG capsules exhibited enhanced T-cell proliferative response after 4 weeks when the response of the group is compared to that of the control group by the Wilcoxon statistical test. These reults therefore show that in healthy individuals, the simultaneous intake of BSS+BSSG leads to potentiated T-cell responses as measured in vitro by the proliferation test.

ANECDOTAL CASES TREATED WITH BSS+BSSG CAPSULES

Case 1: Hashimoto's Thyroiditis:

A. v. Z. a 34 year old Caucasian female was diagnosed clinically and serologically as having Hashimoto's thyroiditis. Blood was drawn and the titer of anti-thyroid autoantibodies was determined by the hemagglutination test. The results obtained at diagnosis were as follows:
Anti-microsomal antibodies: positive (1:1000)
Anti-thyroglobulin antibodies: negative
All other immunological parameters (complement levels, acute phase proteins, and other autoantibodies) were normal.

TABLE XIII

IN VITRO PHA RESPONSES OF T-CELLS FROM HEALTHY
INDIVIDUALS AFTER 4 WEEKS
INTAKE OF BSS + BSSG CAPSULES (60 MG + 0.6 MG RESPECTIVELY)
DAILY
Peripheral blood was obtained from 3 volunteers at baseline and again
after 4 weeks
of BSS + BSSG intake (60 mg BSS + 0.6 mg BSSG daily).
Two volunteers served as
controls since they donated blood but did not receive the capsules. The response
measured is Thymidine uptake by T-cells stimulated with optimal doses of PHA.

| Volunteers | Time = 0 Absolute dpm[a] | Time = 4 weeks Absolute dpm | Absolute Change (Baseline - 4 week) | "p"[b] |
|---|---|---|---|---|
| Group A:* | | | | |
| i) A. le R. | | | | |
| PHA | 110150 | 148590 | 38440 | |
| C/med. | 324 | 3109 | | |
| ii) R. R. | | | | |
| PHA | 106024 | 169024 | 63000 | 0.02 |
| C/med. | 785 | 1152 | | |
| iii) A. L. | | | | |
| PHA | 75842 | 147817 | 71975 | |
| C/med. | 529 | 1604 | | |
| Group B:** | | | | |
| i) J. L. | | | | |
| PHA | 114373 | 124231 | 9858 | |
| C/med. | 587 | 649 | | |
| ii) B.v.d.W. | | | | N.S. |
| PHA | 81823 | 80385 | −1438 | |
| C/med. | 1043 | 1545 | | |

*Group A: individuals were ingesting BSS + BSSG capsules as indicated above.
**Groub B: control group.
[a]Absolute dpm: stimulated dpm - backgroud dpm
[b]Wilcoxon statistical test used to determine difference between day = 0 and 4 week value for each group.

After 6 weeks of treatment with capsules containing 10 mg BSS+0.1 mg BSSG (2 capsules three times a day), the above serological test was repeated and the following results were obtained:
Anti-microsomal antibodies: negative
Anti-thyroglobulin antibodies: negative
The patient had also shown clinical improvement during the same period of time without any other comittent therapy.

Case 2: Atopic Eczema

J. le R. a 31 year old Caucasian female was born with atopic eczema due to a familial history of this condition (her father as well as her grand-father had been known sufferers of atopic eczema). At the age of 16 years, the condition worsened to such an extent (extensive lesions on the hands, feet and behind her knees in the poplital fold) that she had to be treated with cortisone tablets, topical cortisone-based cream as well as injections. The patient found that with time the cortisone treatment did not improve her condition and this got so bad that she took recourse to a homeopath whose treatment did nothing for the condition. Finally the patient's lesions developed secondary bacterial infections and the rest of her body was covered with dry and itchy skin. She was treated with the BSS+BSSG capsules (0.1 mg BSSG+10 mg BSS: 3 capsules per day) and within 6 weeks her lesions had almost disappeared without any other concomitant treatment. After 7 months of the described therapy the lesions which remained were small and limited in extent and these continued to diminish slowly. The dramatic amelioration in this pateint's condition has led to a new mental approach to everyday life since she no longer had to cover her body due to the decrease in the sizes of the eczematous lesions.

I. v. R. a 26 year old Caucasian female had been suffering from relentless atopic eczema in her inguinal areas for over a year. She had been treated by her general practionner who had prescribed topical steroidal cream without any overt improvement in her lesions. She was treated with BSS + BSSG capsules (20 mg. BSS+0.2 mg BSSG; 3 caspules per day) and within 6 weeks of therapy, attested the disappearance of the lesions without the use of concommitant steroidal therapy.

Case 3: Asthma and Recurrent Chest Infections

A female who had been an asthma sufferer for 40 years and who suffered daily attacks necessitating prophylactic therapy, was treated with capsules containing BSS+BSSG (10 mg+0.1 mg respectively; 3 capsules per day) and within a month, there was a noticeable difference in her condition. After a year of treatment, she suffered very few attacks of asthma and when these did occur, they were much lighter and not so exhaustive in nature. It should also be noted that there was no concomitant asthma therapy in conjunction with the BSS+BSSG capsules.

The son of the above-mentioned case inherited a "weak chest" from his mother. In his case he not only suffered from asthma attacks but he was prone to recurrent bronchitis and pneumonia whenever he caught a common cold. He was treated with the same capsules (BSS+BSSG: 10 mg+0.1 mg; 3 capsules per day) and within a year he no longer suffered asthma attacks. Moreover, the frequency and severity of his colds had decreased dramatically. Of particular interest was the outcome of a medical check-up on his immune system: this showed that he had developed a very high degree of immunity to viral and bacterial infections.

Case 4: Arthritis

A sufferer of osteo-arthritis of many years duration had been treated for 2 years with BSS+BSSG capsules (10 mg+0.1 mg respectively) when all visible signs of inflammation had disappeared, especially so in the articulations of his hand thereby restoring, total mobility of all the digits. All the other joints appeared to have escaped the ravages of osteo-arthritis which had been diagnosed unambiguously several times. No other medical treatment had afforded any relief even remotely comparable with that derived from the capsules. The patient also attested to a feeling of well-being since taking the BSS+BSSG capsules.

Another case of arthritis treated with BSS + BSSG capsules is presented. A 53 year old Caucasian female who had suffered from rheumatoid arthritis for 20 years (with complicating clinical osteo-arthritis due to polio in her youth) had been using non-steroidal anti-inflammatories. She was treated with BSS+BSSG capsules: 20 mg BSS+0.2 mg BSSG; 3 capsules per day and within a year, her use of non-steroidal anti-inflammatory bad decreased by up to 65–70% of the original doses with clinical improvements such as the regaining of mobility of her digits, disappearance of pains in he wrists, etc.

Case 5: Psoriasis Trial

Twelve patients with histologically confirmed psoriasis of different types, degrees of severity on different areas of the body were invited to take part in a clinical trial which was evaluated and accepted by the Ethics Committee of the University of Stellenbosch Medical School (91/075) and the Medicines Control Council [26/8/1/2/1 (1017)].

Patients received capsules containing BSS+BSSG as follows:
i) For the first 3 months 3 capsules per day. Each capsule contained 20 mg BSS and 0.2 mg BSSG.
ii) For the second 3 months 8 capsules per day also containing 20 mg BSS and 0.2 mg BSSG each.

Patient's response to treatment was measured using the Psoriasis Area and Severity Index (PASI) method of Fredrikson and Petterson (Dermatologia 157, 238–244, 1978) and was done by a qualified dermatologist.

Table XIV shows the PASI scores of the patients at time zero (PASI 1), after 1 month on BSS + BSSG (PASI 2); after 2 months (PASI 3) and three months (PASI 4). After 3 months, there was a wash-out period of one month and PASI 5 was measured after this. Subsequently the dose was increased from 3 to 8 capsules a day for all except patient N. Garcia, who increased her capsules from 3 to 6 because of low body weight of 50 kg. PASI 6 was measured one month later. It is evident that the PASI scores are much lower in 8 out of 10 patients that proceeded to this stage (2 patients withdrew from the trial). The statistical significance of the lower PASI score is $p=0.009$ and the results are presented graphically in FIG. 4 as the change in mean PASI scores for the 10 patients with time.

No clinical, chemical pathological or haematological side-effects of BSS+BSSG therapy were detected during this study.

Case 6: Cancer

A 40 year old female was diagnosed as having cancer under the tongue. Her teeth were extracted and radiation was given. Her weight dropped from 175 lbs to 130 lbs within a month and shortly afterwards, the lymphoid glands in her neck region enlarged to the size of a small bird's eggs. Her doctor proposed an operation in order to excise the glands but the patient refused and opted for the BSS+BSSG therapy (0.1 mg BSSG+10 mg BSS; 3 capsules per day). Within a month, the glands had softened and 4 months later, one of the glands had totally disappeared while the remaining one was still visible as a small lump. This gland was excised and the histological examination reported the gland to consist of fibrous tissue with a little puss in the centre. The patient continued the treatment for 2 years and since then contact with the patient has been lost.

Another case of cancer treated with the BSS+BSSG capsules is hereby reported. Mrs W., 74 year old, was diagnosed as having an inoperable adeno-carcinoma of the lung. Her doctor proposed palliative radiation although she was in no great pain. The patient heard of the BSS+BSSG treatment from a neighbour and requested such therapy. She was treated with the mixture of BSS+BSSG (10 mg BSS+ 0.1 mg BSSG; 3 capsules per day). After 6 months of this therapy, her persistent cough had disappeared and she continued to take the capsules. Nine years later, she was re-examined and re-X-rayed. The original tumour mass in the lung was still visible and it was proposed by the doctor that her body's defences had killed the tumour and had enclosed it as a solid dead mass of tissue. The patient died 2 years later from a stroke at the age of 85 years.

Another patient (70 years of age) was diagnosed as having lymphoma of the colon with a large irresectable mass in the pelvis. Colostomy was conducted and biopsies of the colon was confirmed by 2 separate pathologists as lymphoma of the colon. The surgeon proposed radiation in order to ease the last few months of the patient's life. This was done and at the same time the patient started BSS+BSSG treatment (2 mg BSS+2 mg

TABLE XIV

PASI EVALUATION OF PSORIASIS PATIENTS ON BSS + BSSG CAPSULES

Twelve patients with active psoriasis were treated with 3 capsules/day containing 20 mg BSS and 0.2 mg BSSG for 3 months (PASI 1, 2, 3 and 4) followed by a month with no medication (PASI 5) and then 8 capsules per day for the next month (PASI 6) except for patient N. G. who took 6 capsules/day due to low body mass of 50 kg. Two patients (J. P. and A. E. C.) elected to leave the trial. PASI is the Psoriasis Area and Severity Index as defined by Fredrikson and Petterson (Dermatologia 157, 238–244, 1978).

| PATIENT | SEX | AGE | DOSE | PASI 1 0 time | PASI 2 1 mnth | PASI 3 2 mnths | PASI 4 3 mnths | PASI 5 4 mnths | PASI 6 5 mnths |
|---|---|---|---|---|---|---|---|---|---|
| A. STEFFAN | F | 35 | 3 caps/day/3 mths 8 caps/day end | 7,0 | 5,0 | 5,0 | 4,7 | 5,0 | 4,8 |
| E. MARAIS | M | 53 | 3 caps/day/3 mths 8 caps/day end | 5,8 | 4,8 | 5,4 | 5,5 | 3,6 | 3,8 |
| C. SWART | F | 36 | 3 caps/day/3 mths 8 caps/day end | 4,6 | 5,2 | 4,0 | 4,4 | 3,3 | 3,5 |
| J. COOKE | M | 41 | 3 caps/day/3 mths 8 caps/day end | 1,0 | 0,6 | 0,6 | 0,4 | 1,2 | 1,2 |
| J. PRINCE | F | 26 | 3 caps/day/3 mths 8 caps/day end | 1,8 | 2,0 | 2,4 | 1,8 | 1,2 | Rx stopped |
| G. KENNETT | M | 35 | 3 caps/day/3 mths 8 caps/day end | 2,5 | 2,7 | 3,1 | 2,4 | 2,0 | 2,6 |
| *N. GARCIA | F | 14 | 3 caps/day/3 mths 6 caps/day end | 5,6 | 5,8 | 4,0 | 4,3 | 2,8 | 3,6 |
| J. H. SNYMAN | M | 41 | 3 caps/day/3 mths 8 caps/day end | 4,5 | 2,6 | 3,6 | 2,6 | 2,6 | 2,4 |
| T. GELDENHUYS | M | 20 | 3 caps/day/3 mths 8 caps/day end | 4,7 | 3,9 | 4,6 | 5,0 | 4,2 | 3,6 |
| M. A. VILJOEN | F | 44 | 3 caps/day/3 mths 8 caps/day end | 3,2 | 2,6 | 3,0 | 3,1 | 1,8 | 2,4 |
| F. A. KING | F | 36' | 3 caps/day/3 mths 8 caps/day end | 3,5 | 3,3 | 2,5 | 2,9 | 2,4 | 3,2 |
| A. E. LOOTS | F | 30 | 3 caps/day/2 mths | 5,5 | 4,8 | 5,9 | Rx stopped | | |

PASI 1: BEFORE Rx
PASI 2, 3, 4: 3 CAPS/DAY
PASI 5, 6, 7: 8 CAPS/DAY
*6 CAPS/DAY

BSSG precipitated onto 200 mg talcum; 3 per day). Four months later the patient returned to the surgeon in improved health and to complain of the inconvenience of the colostomy. X-rays were taken and it was decided to reverse the colostomy. During the operation, the large irresectable mass was still in evidence and a biopsy taken of the mass was conducted. The report was given as a benign mass. The original slides of the tumour mass was re-confirmed by an independent pathologist as lymphoma of the colon. Nineteen years later, the patient is still alive and in good health and is now well into his eighties.

DISCUSSION

The data presented here show that the functions of T-cells can be modulated both in vitro and in vivo by phytosterols and phytosterolins in a ratio of between of 1:1 to 500:1 BSS to BSSG. These cells exhibit enhanced proliferative responses when co-cultured with BSS and BSSG and under the same conditions, the cells are shown to enhance their secretion of important lymphokines such as Interleukin 2 and Gamma Interferon. On the other hand, B-cells are inhibited when cultured with the compounds. The activity of NK cells in vitro are significantly enhanced in the presence of BSS+BSSG. It is therefore feasible to say that phytosterols and phytosterolins modulate the functions of both T- and B-cells and NK cells to such an extent that immune homeostasis and normalization of a defective immune system could ensue following the intake of the phytosterols and phytosterolins. At this time it is believed that the following clinical implications of the data obtained may be expected:

1) Certain congenital or acquired immunodeficiencies (e.g. common variable immunodeficiency or C.V.I.) where both T- and B-cells are present but these cells are sub-optimally active. In such cases, BSS and BSSG would be beneficial since the phytosterols would act on the T-cell compartment and enhance their functions. The in vitro data showed that the secretion of important T-cell derived lymphokines were enhanced when T-cells were stimulated simultaneously with the phytosterols and phytosterolins and the same cells expressed higher levels of membrane antigens involved in cell proliferation. Under such potentiated conditions, we can expect that in cases of hypogammaglobulinaemia due to defective T-cell functions (lymphokine secretion and/or membrane antigen expression) the intake of phytosterols and phytosterolins in the proportions described above would lead to normalization of the T-cell functions and the secretion of normal levels of immunoglobulins in vivo.

2) Chronic and acute viral and bacterial infections that are not dependent on T-cell proliferation for viral replication and where T-cell proliferation is necessary for the inhibition of viral replication. The in vitro data presented showed that BSS and/or BSSG enhanced the activity of NK cells. In cases of chronic viral infections due to viral latency or defective immune responses, patients would benefit from the intake of the phytosterols and phytosterolins. The anecdotal case of the patient suffering from recurrent pneumonia and bronchitis having exhibited enhanced resistance to bacterial and viral secondary infections is a good example of the benefits to be derived from the intake of the phytosterols and phytosterolins.

3) Autoimmune diseases are characterised by, firstly, the polyclonal activation of B-cell clones producing autoantibodies and, secondly, abnormal T-cell regulatory mechanisms. In such instances, the immunomodulation of T-cells by BSS and BSSG would therefore meet these requirements. Also, since the phytosterols inhibit the proliferation of B-cells in vitro, the compounds would inhibit the activation of autoreactive B-cell clones and thereby decrease the release of autoantibodies from such plasma cells. The anecdotal case of Hashimoto's thyroiditis reverting to seronegativity within 6 weeks of treatment is one example of such an autoimmune disease where the phytosterols and phytosterolins have a beneficial effect. The other cases of rheumatoid arthritis and osteo-arthritis (also autoiummune diseases) who showed clinical improvement following BSS+BSSG intake would seem to confirm this claim.

4) Psoriasis: The results of the clinical trial presented would indicate that this condition would benefit from the use of BSS+BSSG treatment as outlined in the report. Psoriasis is a condition in which several immunological abnormalities have been described (defective T-cell responses in vivo as well as in vitro; defective lymphokine secretion; etc. ) and it is foreseeable that the intake of the phytosterols and phytosterolins could improve the immunological defects with improvement of the clinical conditions of the patients.

5) Atopic ezcema and Asthma: This condition is characterised by gross abnormalities in the immune regulatory mechanisms. These include abnormal secretion of Gamma Interferon and IL-2 with increased synthesis of IgE antibodies by the B-cells. The in vitro data presented shows that the phytosterols and phytosterolins inhibit B-cell proliferation while enhancing the function of T-cells (enhanced secretion of lymphokines such as IL-2 and Gamma Interferon). Such immunomodulatory properties of the phytosterols and phytosterolins are important in the treatment of atopic eczema as well as asthma. Furthermore, the anecdotal cases presented attest to the beneficial effects of the BSS+BSSG capsules.

6) Tumours: The data presented in this report showed that the activity of T-cells as well as that of NK cells was greatly enhanced in the presence of the phytosterols and phytosterolins. In clinical cases of cancer, it is known that a general state of immunosuppression exists (abnormal activity of T-cells, defective secretion of important lymphokines, etc.) thereby facilitating the progression of the tumour mass. It is conceivable that the intake of BSS+BSSG would normalize in vivo certain immunological mechanisms such as normalization of the secretion of IL-2 and Gamma Interferon and enhance the cytotoxic activities of the NK cells as well as that of the T-cytotoxic cells which carry out the concept of immunosurveillance. The anecdotal cases of cancer presented confirm this hypothesis.

We claim:

1. A method for the treatment of diseases caused by perturbations of normal lymphocyte homeostasis, comprising administering to a human suffering from a said disease an effective amount of a mixture of β-sitosterol (BBS) and β-sitosterol glucoside (BSSG) in a ratio of from 1:1 to 200:1.

2. A method according to claim 1, in which said ratio is 100:1.

3. A method according to claim 1, for the treatment of common variable immunodeficiency.

4. A method according to claim 1, for the treatment of a vital or a bacterial infection which is not dependent on T-cell proliferation for viral replication and wherein T-cell proliferation is necessary for inhibiting viral replication.

5. A method according to claim 1, for the treatment of a disease due to polyclonal activation of B-cell clones producing autoantibodies and an abnormal T-cell regulatory mechanism.

6. A method according to claim 1, wherein said disease is Hashimoto's thyroiditis.

7. A method according to claim 1, wherein said disease is rheumatoid arthritis.

8. A method according to claim 1, wherein said disease is osteo-arthritis.

9. A method according to claim 1, wherein said disease is psoriasis.

10. A method according to claim 1, wherein said disease is atopic eczema or asthma caused by gross abnormalities in immune regulatory mechanisms.

11. A method according to claim 1, wherein said disease is defective lymphokine secretion by T-cells or excess production of IgE by B-cells.

12. A method according to claim 1, wherein said disease is the enhanced activity of NK cells or increased secretion of IL-2 and Gamma Interferon by T-cells.

* * * * *

UNITED STATES PATENT AND TRADEMARK OFFICE
CERTIFICATE OF CORRECTION

PATENT NO. : 5,486,510
DATED : January 23, 1996
INVENTOR(S) : Patrick Jacques Desire BOUIC et al.

It is certified that error appears in the above-indentified patent and that said Letters Patent is hereby corrected as shown below:

On the title page, in Item [75], change the surname of the second inventor from "De Vosa Albrecht" to --De Vos Albrecht--.

Signed and Sealed this

Ninth Day of April, 1996

Attest:

BRUCE LEHMAN

Attesting Officer

Commissioner of Patents and Trademarks